(12) United States Patent
Jackson et al.

(10) Patent No.: US 8,853,360 B2
(45) Date of Patent: Oct. 7, 2014

(54) ENGINEERED BOTULINUM NEUROTOXIN C1 WITH SELECTIVE SUBSTRATE SPECIFICITY

(75) Inventors: Meyer B. Jackson, Madison, WI (US); Dongsheng Wang, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 326 days.

(21) Appl. No.: 13/167,156

(22) Filed: Jun. 23, 2011

(65) Prior Publication Data

US 2011/0318385 A1 Dec. 29, 2011

Related U.S. Application Data

(60) Provisional application No. 61/357,713, filed on Jun. 23, 2010.

(51) Int. Cl.

| | | |
|---|---|---|
| C07K 1/00 | (2006.01) | |
| C07K 14/00 | (2006.01) | |
| C07K 17/00 | (2006.01) | |
| C12Q 1/02 | (2006.01) | |
| A61K 39/08 | (2006.01) | |
| C07H 21/04 | (2006.01) | |
| C07K 14/33 | (2006.01) | |

(52) U.S. Cl.
CPC ............ *C07K 14/33* (2013.01); *G01N 2333/33* (2013.01)
USPC ................ 530/350; 424/239.1; 424/247.1; 435/29; 435/172.1; 435/172.3; 536/23.7

(58) Field of Classification Search
None
See application file for complete search history.

(56) References Cited

U.S. PATENT DOCUMENTS 7,172,764 B2 * 2/2007 Li et al. ............... 424/239.1

OTHER PUBLICATIONS

Bowie et al. (Science, 1990, 257:1306-1310).*
Lam, P.L., et al., "Transgenic Mouse Overexpressing Syntaxin-1A as a Diabetes Model" (2005) Diabetes 54, 2744-2754.
Ng, B., et al., "Syntaxin-1A inhibition of P-1075, cromakalim, and diazoxide actions on mouse cardiac ATP-sensitive potassium channel" (2008) Cardiovascular Research 80, 365-374.
Jin, R. et al., "Structural and biochemical studies of botulinum neurotoxin serotype C1 light chain protease: implications for dual substrate specificity" (2007) Biochemistry 46 (37), 10685-10693.
Breidenbach, M.A., et al., "Substrate recognition strategy for botulinum neurotoxin serotype A" (2004) Nature 432: 925-929.
Dong, M., et al.,"Mechanism of botulinum neurotoxin B and G entry into hippocampal neurons" (2007) J Cell Biol 179, 1511-1522.
Gascon, S., et al., "Dual-promoter lentiviral vectors for constitutive and regulated gene expression in neurons" (2008) J Neurosci Methods 168, 104-112.
Binz, T., et al., "Arg(362) and Tyr(365) of the botulinum neurotoxin type a light chain are involved in transition state stabilization" (2002) Biochemistry 41, 1717-1723.

* cited by examiner

*Primary Examiner* — Gary Nickol
*Assistant Examiner* — Lakia Tongue
(74) *Attorney, Agent, or Firm* — Quarles & Brady LLP (57) ABSTRACT

An isolated polypeptide comprising a botulinum neurotoxin C1 light chain having a modified amino acid sequence relative to the sequence of a wild-type botulinum neurotoxin C1 light chain is disclosed. The modified botulinum neurotoxin C1 light chain is capable of selectively cleaving syntaxin protein, but has substantially reduced or no activity against SNAP-25 as compared to wild type botulinum neurotoxin C1 light chain, and is thus useful as a research tool and in medical treatment.

5 Claims, 6 Drawing Sheets

ENGINEERED BOTULINUM NEUROTOXIN C1 WITH SELECTIVE SUBSTRATE SPECIFICITY

CROSS-REFERENCE TO RELATED APPLICATION

This application claims the benefit of U.S. Provisional Patent Application No. 61/357,713 filed on Jun. 23, 2010, which is incorporated by reference herein in its entirety.

STATEMENT REGARDING FEDERALLY SPONSORED RESEARCH OR DEVELOPMENT

This invention was made with government support under NS044057 and NS059854 awarded by the National Institutes of Health. The government has certain rights in the invention.

FIELD OF THE INVENTION

This invention relates generally to the clostridial neurotoxin botulinum serotype C protein (BoNT/C). In particular, the present invention is directed to an engineered mutant of wild type BoNT/C1 having surprisingly selective substrate specificity, wherein the mutant cleaves the syntaxin protein, but has substantially reduced or no activity against SNAP-25 protein as compared to the wild type BoNT/C1.

BACKGROUND OF THE INVENTION

*Clostridium botulinum* is a spore forming, obligate anaerobic bacterium that naturally resides in soil. All *C. botulinum* subgroups produce botulinum neurotoxins (BoNTs), which generally act to impair synaptic transmission and are effective in curtailing uncontrolled muscle contractions. Accordingly, botulinum neurotoxins have many important therapeutic, medical, and cosmetic applications.

BoNTs act by cleaving and inactivating proteins that function in neurotransmitter release at synapses. Neurotransmitter release involves exocytosis, whereby synaptic vesicles filled with neurotransmitter fuse with the plasma membrane of a nerve terminal. This process is mediated by the assembly of a synaptic fusion complex, which is comprised of a set of soluble N-ethylmaleimide-sensitive factor (NSF) attachment protein receptors (SNARE proteins). BoNTs target three different SNARE proteins that perform functions essential for membrane fusion and successful neurotransmitter release at the synapse: syntaxin, SNAP-25 and synaptobrevin.

The seven different BoNT serotypes are designated by the letters A through G. In particular, BoNT/C1, which has a structure similar but not identical to other BoNT serotypes, is composed of a 100 kD heavy chain and a 50 kD light chain. The heavy chain binds to the surface of a cell by recognizing a receptor. After binding, the light chain translocates across the membrane and enters the cell. The light chain contains a zinc dependent endopeptidase which is responsible for the catalytic cleavage of the target SNARE proteins.

BoNT/A and BoNT/E cleave SNAP-25, while BoNT/B, BoNT/D, BoNT/F, and BoNT/G cleave synaptobrevin. BoNT/C1 is unique in that it cleaves both SNAP-25 and syntaxin; thus it is the only known BoNT that cleaves syntaxin, and it is the only known BoNT having dual substrate specificity. BoNT/C1 cleaves SNAP-25 at the bond between Arg198 and Ala199 (one residue before the BoNT/A cleavage site between Gln197 and Arg198), and syntaxin at the bond between Lys253 and Ala254. There are two isoforms of syntaxin, designated 1A and 1B, and BoNT/C1 cleaves them both at the same site.

Although there are BoNTs that specifically cleave synaptobrevin and SNAP-25, none of the naturally occurring BoNTs cleave only syntaxin. A protein that targets syntaxin while not affecting SNAP-25 or other SNARE protein activity would be a powerful research tool for neurophysiologists studying the role of specific proteins such as syntaxin in neurotransmission.

Furthermore, recently published research suggests that fluctuating levels of syntaxin may be correlated to glucose intolerance and diabetes, as well as possibly being associated with a broad range of neurological disorders, such as Williams Syndrome, schizophrenia, and severe depression (Lam, P. P. L., Y. Leung, L. Sheu, J. Ellis, R. G. Tsuchima, L. R. Osborne, and H. Y. Gaisano, Diabetes (2005) 54, 2744-2754). In addition, other research has indicated that fluctuations of syntaxin levels in the myocardium may affect the therapeutic effectiveness of ATP sensitive potassium channel openers (Ng, B., Y. Kang, H. Xie, H. Sun, and H. Gaisano, Cardiovascular Research (2008) 80, 365-374). Thus, an entity that specifically targets syntaxin for cleavage while not affecting other biological targets could potentially have utility as a therapeutic agent.

SUMMARY OF THE INVENTION

By creating a large library of mutant BoNT/C1 light chain polypeptides and assaying the substrate specificity of the library members directly in neurons, the inventors have discovered a class of novel mutant BoNT/C1 light chain polypeptides having unique substrate selectivity as compared to the wild type, such that they cleave syntaxin but have substantially reduced or no activity against SNAP-25. Accordingly, the invention encompasses such novel BoNT/C1 polypeptides and compositions containing the polypeptides, isolated nucleic acids that encode for such polypeptides, as well as methods of using such novel polypeptides as research tools and in medical treatments.

In a first aspect, the invention encompasses an isolated polypeptide comprising a botulinum neurotoxin C1 light chain having a modified amino acid sequence relative to the amino acid sequence of a wild-type botulinum neurotoxin C1 light chain, wherein the modified botulinum neurotoxin C1 light chain is capable of selectively cleaving syntaxin protein but has substantially reduced or no activity against SNAP-25, as compared to the wild-type botulinum neurotoxin C1 light chain. In certain preferred embodiments, the modified amino acid sequence is modified in the catalytic cave-S1' pocket or the substrate binding region of the wild-type botulinum neurotoxin C1 light chain.

Preferably, the wild-type botulinum neurotoxin C1 light chain that is modified has the amino acid sequence set forth in SEQ ID NO:1. In certain embodiments, the catalytic cave-S1' pocket is modified at amino acid residues L200, M221, and I226 of the wild-type botulinum neurotoxin C1 light chain. Preferably, the modifications of amino acids L200 and M221 are the amino acid substitutions L200W and M221W. Preferably, the modification of amino acid residue I226 is an amino acid substitution selected from the group consisting of I226W, I226L, I226K, and I226H.

In other embodiments, the substrate binding region is modified at one or more of amino acid residues F50, S51, R52, or N53 of the wild-type botulinum neurotoxin C1 light chain. Preferably, the modifications comprise one or more of the amino acid substitutions S51T, R52N, and N53P.

This aspect further encompasses compositions containing both the isolated polypeptide as described above and a carrier. In addition, this aspect includes isolated nucleic acids encoding the isolated polypeptides described above.

In a second aspect, the invention encompasses a method of studying the function of syntaxin in a cell. The method includes the steps of contacting the cell with a composition that includes the polypeptide as described above, and assaying a function of syntaxin in the cell. Preferably, the cell that is contacted with the composition is a neuron. The cell may be contacted in vitro or in vivo.

In a third aspect, the invention encompasses a method of selectively cleaving syntaxin protein relative to SNAP-25 in a cell. The method includes the steps of contacting a cell with the isolated polypeptide as described above in the first aspect. After such contact, the syntaxin protein is selectively cleaved in the cell relative to SNAP-25 by the isolated polypeptide. Preferably, the cell that is contacted with the isolated oolypeptide is a neuron. The cell may be contacted in vitro or in vivo.

Other objects, features and advantages of the present invention will become apparent after review of the specification, claims and drawings.

BRIEF DESCRIPTION OF THE DRAWINGS

FIG. 3 shows the results of SDS polyacrylamide gel electrophoresis/western-blot analysis using antibodies against SNAP-25 and syntaxin for both uninfected cultured rat hippocampal neurons ("neuron") and cultured rat hippocampal neurons exposed to lentiviral vectors expressing wild type and four additional mutant BoNT/C1 light chains. The lane labeled "51T-52N-53P" shows the results for the mutant BoNT/C1 light chain having the amino acid substitutions S51T, R52N, and N53P relative to the wild type light chain (SEQ ID NO:1). The three rightmost lanes show the results for three different triple mutant BoNT/C1 light chains having amino acid substitutions at residues 220 and 221 (L220W/M221W) of the wild type light chain of SEQ ID NO:1 and additionally having a third amino acid substitution at residue 226 (from left to right: I226L, I226K, and I226H).

FIG. 4 shows SDS polyacrylamide gel quantification of BoNT/C1 cleavage for both syntaxin (FIG. 4A) and SNAP-25 (FIG. 4B). "Control" shows results from untransfected cultured rat hippocampal neurons; "BoNT/C1-wt" shows results from cultured rat hippocampal neurons exposed to lentiviral vectors expressing wild-type BoNT/C1 light chain (SEQ ID NO:1); "BoNT/C1-α51" shows results from cultured rat hippocampal neurons exposed to lentiviral vectors expressing wild-type BoNT/C1 light chain having the amino acid substitutions S51T/R52N/N53P; "BoNT/C1-α3W" shows results from cultured rat hippocampal neurons exposed to lentiviral vectors expressing wild-type BoNT/C1 light chain having the amino acid substitutions L200W/M221W/I226W; "BoNT/C1-γ" shows results from cultured rat hippocampal neurons exposed to lentiviral vectors expressing wild-type BoNT/C1 light chain having the amino acid substitutions R372A/Y375F. Band densities were reduced by cleavage in parallel with the appearance of lower-molecular mass cleavage products. Syntaxin and SNAP-25 signals were normalized to the β-actin control and averaged (N=3). $p<0.05$ (one asterisk).

FIG. 5A: Miniature excitatory synaptic currents (mEPSCs). FIG. 5B: Synaptic currents evoked by extracellular stimulation (200 µA, 0.4 ms). FIG. 5C: Mean mEPSC frequency (N=8-10 cells; ~20-300 events per cell). FIG. 5D: Mean mEPSC amplitude. FIG. 5E: Mean evoked synaptic current. FIG. 5F: Mean mEPSC charge. $p<0.01$ (two asterisks); $p<0.001$ (three asterisks). Infective agents: Control, none; BoNT/C1-wt, vectors expressing wild-type BoNT/C1 light chain (SEQ ID NO:1); BoNT/C1-α51, vectors expressing wild-type BoNT/C1 light chain having the amino acid substitutions S51T/R52N/N53P; BoNT/C1-α3W, vectors expressing wild-type BoNT/C1 light chain having the amino acid substitutions L200W/M221W/I226W; BoNT/C1-γ, vectors expressing wild-type BoNT/C1 light chain having the amino acid substitutions R372A/Y375F.

FIG. 6A: Amperometric traces, with exocytosis induced by application of 105 mM KCl (bar below). FIG. 6B: Cumulative spike counts from traces such as in panel A (control; N=9-16 cells). FIG. 6C: Mean frequency of spikes per cell. $p<0.001$ (asterisks).

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably. The term "polypeptide" and the term "protein" are used interchangeably herein.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The following abbreviations are used herein: BoNT, botulinum neurotoxin protein; PAGE, polyacrylamide gel electrophoresis; SDS, sodium dodecyl sulfate; WT, wild type. The art-accepted standard single letter amino acid codes are used herein to identify specific amino acids and the amino acid substitutions of the present invention.

II. The Invention

The inventors have discovered that modifying the amino acid sequence of wild type BoNT/C1 light chain in either the catalytic cave-S1' pocket or the substrate binding region can result in a novel neurotoxin C1 light chain with altered substrate specificity. Specifically, the inventors have created modified BoNT/C1 light chain polypeptides that are capable of cleaving syntaxin protein but have substantially reduced or no activity against SNAP-25.

As outlined in more detail in the Example below, the inventors used the crystal structure previously reported for BoNT/C (see Jin, R. et al., Biochemistry 46 (37), 10685-10693 (2007); structure summary also published as NCBI MMDB ID: 59509, PDB ID: 2QN0) in structure-based modeling to identify target regions for site-directed mutagenesis to potentially alter the substrate specificity of the BoNT/C1 light chain. Specifically, the inventors identified two regions of the BoNT/C1 light chain for targeting: a region in the catalytic cave S1' pocket and a substrate binding region. The inventors then used site-directed mutagenesis to generate 150 mutant BoNT/C1 light chain polypeptides and screened the mutants for substrate specificity in neurons. Two series of mutations improved the substrate specificity of the BoNT/C1 light chain such that the mutant cleaved syntaxin but not SNAP-25.

Accordingly, in a first aspect, the invention encompasses an isolated polypeptide containing a botulinum neurotoxin C1 light chain having a modified amino acid sequence relative to the sequence of a wild-type botulinum neurotoxin C1 light chain, wherein the modified botulinum neurotoxin C1 light chain is capable of cleaving syntaxin protein but has substantially reduced or no activity against SNAP 25, as compared to the wild-type botulinum neurotoxin C1 light chain. The invention further encompasses an isolated nucleic acid sequence coding for such polypeptides.

The isolated polypeptide of the invention preferably has an amino acid sequence that is modified in either the catalytic cave-S1' pocket or the substrate binding region of the botulinum neurotoxin C1 light chain. Preferably, the wild-type botulinum neurotoxin C1 light chain that is modified has the amino acid sequence set forth in SEQ ID NO:1 (NCBI accession no. 2QN0_A, GI: 158430347; Jin, R. et al., Biochemistry 46 (37), 10685-10693 (2007)).

The S1' pocket of the wild-type botulinum neurotoxin C1 light chain includes residues Pro168, Leu200, Met221, Ile226, His229, and Arg372 (see Jin, R. et al., Biochemistry 46 (37), 10685-10693 (2007); NCBI MMDB ID: 59509). In embodiments where the wild-type botulinum neurotoxin C1 light chain has the amino acid sequence set forth in SEQ ID NO:1 and where the catalytic cave-S1' pocket is modified, it is further preferred that the modification includes three amino acid substitutions at residues 200, 221, and 226 of the wild-type botulinum neurotoxin C1 light chain. At residue 200, the amino acid tryptophan is preferably substituted for cysteine (L200W), and at residue 221, the amino acid tryptophan is preferably substituted for methionine (M221W). At residue 226, the amino acid isoleucine is preferably substituted by one of the group consisting of tryptophan (I226W), leucine (I226L) lysine (I226K), and histidine (L226H).

The substrate binding region includes residues Phe 50, Ser51, Arg52, and Asn53 (not previously reported). Surprisingly, the inventors' data and analysis show that this region is uniquely important for SNAP25 activity. Accordingly, in embodiments where the wild-type botulinum neurotoxin C1 light chain has the amino acid sequence set forth in SEQ ID NO:1 and where the substrate binding region is modified, it is further preferred that the modification includes an amino acid substitution at one or more of the amino acid residues 50, 51, 52, and/or 53 of the wild-type botulinum neurotoxin C1 light chain. In an especially preferred embodiment, the modification is the three residue mutation of the wild-type botulinum neurotoxin C1 light chain, S51T/R52N/N53P.

Methods for mutating proteins are well-known in the art. For the present invention, it is preferable to perform site-directed mutagenesis on the DNA encoding the BoNT. A number of mutagenesis kits are known in the art and commercially available. As a non-limiting example, the inventors used the QuikChange II XL Site-Directed Mutagenesis Kit, Agilent Technologies, Inc., Santa Clara, Calif. In this manner, and using the guidance provided herein, one of skill in the art can make mutations to the codons encoding the amino acids at the targeted sites and specific residues of the BoNT. Preferred methods for manipulation and mutation of nucleotides, as well as for the expression of recombinant peptides, are contained in standard references, such as Sambrook et al., Molecular Cloning: A Laboratory Manual, Second Edition, Cold Spring Harbor Laboratory Press, 1989.

This aspect of the invention also encompasses compositions containing an isolated polypeptide as described above and a carrier. The carrier may be a solvent or other substance suitable for facilitating the transport of the isolated polypeptide or for contacting the isolated polypeptide with a surface, including without limitation a cell membrane or cell wall.

The modified polypeptides described above cleave syntaxin, preventing it from performing its intended function. Based on the assays that have been performed so far, the modified polypeptides apparently do not affect other proteins. No other known agent exhibits this particular substrate selectivity. Accordingly, in a second aspect, the invention encompasses a method of studying the function of syntaxin in a cell.

The method includes the step of contacting one or more cells with a composition containing the modified BoTN/C1 light chain polypeptide, as described above. The cells may be contacted in vitro or in vivo. Contact further includes gaining entry into a cell to provide access of the polypeptide to the target intracellular protein (syntaxin). Preferably, the one or more cells contacted with the composition are neurons. By assaying the effects of the composition on cell function and on various biochemical and molecular pathways, the skilled artisan can learn a great deal about the function of syntaxin at both the cellular and molecular levels.

As a non-limiting example, BoNT/C1 application to neurons causes cell death, while BoNT/A application does not. The modified polypeptides of the present invention will cleave only syntaxin, helping researchers to determine if cell death is abolished by sparing SNAP-25. In another non-limiting example, syntaxin 1A and 1B double knockout mice die embryonically, making it very difficult to prepare cells and tissues lacking these proteins. Using the engineered polypeptides of the present invention as a research tool provides an alternative method of controlling syntaxin levels after cells have been isolated from a wild type animal.

It is further envisioned that the engineered BoNT/C1 polypeptides of the present invention will have utility in a variety of medical applications. Engineered BoNT/C1 can be used in ways similar to uses of BoNT/A, as well as in unique ways that depend on cleavage of syntaxin. Both BoNT/C1 and BoNT/A target the exocytotic apparatus (i.e. the SNARE proteins). By engineering BoNT/C1 to recognize different components of the exocytotic apparatus, medical researchers will be able to develop alternative strategies in which BoNT/C1 can mimic BoNT/A, but with subtle and important differences. Because BoNT/C1 and BoNT/A employ different heavy chains, engineered BoNT/C1 can also be used to target cell types and tissues different from those targeted by BoNT/A.

As non-limiting examples, engineered BoNT/C1 could be used in human patients who may benefit from treatment with BoNT/A, but who have developed BoNT/A resistance. In addition, compared with wild type BoNT/C1, the engineered BoNT/C1 of the present invention will spare SNAP-25, making treatment with the BoNT/C1 of the invention less toxic than treatment with wild type BoNT/C1.

It is known that syntaxin has cell functions apart from exocytosis. For example, it is involved in ion channel regulation, such as the regulation of $K_{ATP}$ channels and calcium channels. Regulation of $K_{ATP}$ channels is very important in type II diabetes treatment. Type II diabetes often results from over stimulation of beta-cells, and treatment often involves stimulating $K_{ATP}$ channels to reduce beta cell electrical activity. Syntaxin 1A down-regulates $K_{ATP}$ channels, which makes cells more excitable. Cleavage of syntaxin will counteract this down-regulation, making $K_{ATP}$ channels spend more time in their open conducting state, and thus reduce insulin secretion by beta cells. Thus, the engineered BoNT/C1 of the present invention has utility as a treatment for diabetes.

In a third aspect, the invention encompasses a method of selectively cleaving syntaxin protein relative to SNAP-25 in a cell. The method includes the step of contacting a cell with an isolated polypeptide as described above. As a result of such contact, syntaxin protein is selectively cleaved in the cell relative to SNAP-25 by the isolated polypeptide. The cell may be contacted with the polypeptide in vivo or in vitro. Preferably, the cell contacted with the polypeptide is a neuron.

The embodiments described here and in the following examples are for illustrative purposes only, and various modifications or changes apparent to those skilled in the art are included within the scope of the invention. The terminology used to describe particular embodiments is not intended to limit the scope of the present invention, which is limited only by the claims. The following example is offered to illustrate, but not to limit, the scope of the present invention.

III. Examples

Example 1

Generation of BoNT/C1 Mutants and Demonstration of Altered Substrate Specificity 1. Materials and Methods In General.

The wild type BoNT/C1 light chain structure was analyzed and the target sites were chosen and mutated. The vectors containing the mutated BoNT/C1 light chain were expressed by lenti-viral vector in cultured hippocampal neurons. After 72 hr-120 hrs expression, the cell lysate was collected and subject to SDS-PAGE. Western-Blot were conducted with specific antibody and the results were analyzed with western-blots.

Target Site Selection.

By studying the crystal structure of BoNT/A light chain (Breidenbach, M. A., and Brunger, A. T., Nature (2004) 432: 925-929; NCBI MMDB ID 31663, PDB ID: 1×TG), we identified regions that could affect the substrate specificity. The crystal structure of BoNT/C1 light chain and BoNT A light chain are similar, so some features are shared between them. The BoNT/A light chain crystal structure also contains the substrate SNAP25, so the interaction between BoNT/A light chain and SNAP25 can be analyzed according to the structure.

Site-Directed Mutagenesis and Mutant Library Preparation.

The inventors used the mutagenesis kit—QuikChange II XL Site-Directed Mutagenesis Kit (Agilent Technologies, Inc., Santa Clara, Calif.) to perform mutations in the DNA coding sequence of the wild type BoNT/C1 light chain to generate 150 mutant BoNT/C1 polypeptides, which were further tested as indicated below. The specific mutants generated and tested are listed below in Table 1.

Protein Purification.

Lysates from cultured neurons were prepared by first washing cells with PBS. Then, 100 µl of lysis buffer (PBS with 1% Triton X-100, 0.05% SDS, and protease inhibitor cocktails) was added per coverslip. The lysates were collected and then vibrated for 10 minutes and centrifuged for 10 min. The supernatants were collected and incubated with SDS loading dye containing 1 mM DTT at 95 degrees centigrade for 5 minutes, and then subjected to SDS-PAGE analysis.

Protein Expression.

To test the substrate specificity of wild type and mutant BoNT/C1, we expressed both wild type and mutant BoNT/C1 light chain in cultured rat hippocampal neurons using lentiviral vectors. 72-120 hours after infection with vector expressing BoNT/C1 light chain, cell lysate was collected, resolved with SDS-PAGE, and subjected to western-blot analysis with antibodies against SNAP-25 and syntaxin. The results of the expression assays for all the mutant BoNT/C1 in the library of mutants are summarized in Table 1 below.

Plasmid Construction and Lenti-Virus Preparation.

The BoNT/C1 light chain (Genebank Number X53751.1, residues 1-449) had been subjected to codon optimization in mammalian cells by GenScript (see Dong, M., et al., *J Cell Biol* 179 (2007), 1511-1522). Site-directed mutagenesis was performed on the BoNT/C1 light chain in a syn-lox lenti-viral vector (see Gascon, S., et al., *J Neurosci Methods* 168 (2008), 104-112). The syn-lox construct, along with two other viral envelope protein encoding vectors, VSVg and delta 8.9, were co-transfected into HEK cells using calcium phosphate. The HEK cells were cultured for another 3-4 days to grow up lentivirus. The supernatant was collected, filtered to remove cell particles, centrifuged at 20,000 rpm for two hours to concentrate the virus, and dissolved in 100 µl PBS (Cellgro, 21-040-CV; Manassas Va.) per 30 ml supernatant.

Protein Expression and Western Blot.

For BoNT/C1 LC expression, 5 µl lenti-virus-PBS was added to each well of a 24-well plate of cultured hippocampal neurons at 10-12 days in vitro. After 72-96 hours, lysates from cultured neurons were prepared by first washing cells with PBS. Lysis buffer (100 µl 1% Triton X-100, 0.05% SDS, and protease inhibitors in PBS) was added and lysates were collected, vibrated for 10 minutes, and centrifuged for 10 min. The supernatants were collected and incubated with SDS loading dye containing 1 mM DTT at 95° C. for 5 minutes. Samples were subjected to SDS-PAGE and blotted with antibodies against SNAP-25 (C1. 71.1, SySys, Gottingen, Germany) and syntaxin (HPC-1, SySys). Monoclonal antibody against β-actin was purchased from Abcam (ab6276-100). Expression in PC12 cells was achieved by electroporation (ECM 830; BTX, Hawthorne N.Y.) of the lenti-viral syn-lox DNA.

Cell Culture.

For primary cultured hippocampal neurons, hippocampi from E-18 embryonic rats were dissected and digested with trypsin for 30 minutes followed by trituration. The cell suspension was plated on poly-D-lysine coated cover slips in Neurobasal-A Medium (600 µl/well of a 24-well plate) together with B27 and 2 mM Glutamax, and culture in a humidified 95% air/5% $CO_2$ incubator. PC12 cells were cultured in DMEM, 5% horse serum, and 5% iron-supplemented calf serum in 10 cm plates at 37° C. in 90% air/10% $CO_2$.

Table 1 lists the specific mutants that were assayed, as well as the results for both the syntaxin and SNAP-25 activity assays. The relative activity for each assay is marked by +, the '+++++' 5 plus means full activity, with fewer pluses indicating less activity; the 'o' means no detectable activity. For specific mutants of interest, the results are discussed in more detail in the "Results and Discussion" section below.

TABLE 1

Expression Assay Results for BoNT/C1 Mutants

| Domain | Mutation | Syntaxin activity | SNAP-25 activity |
|---|---|---|---|
| transition state | 372A | o | o |
|  | 372A-375F (BoNT/C1γ) | o | o |
| S1 pocket | 200W | +++ | +++ |
|  | 200E | +++ | +++ |
|  | 200R | +++ | +++ |
|  | 221W | +++ | +++ |
|  | 221E | +++ | +++ |
|  | 221R | +++ | +++ |
|  | 226A | +++++ | +++++ |
|  | 226C | +++++ | ++++ |
|  | 226D | ++++ | ++ |
|  | 226E | +++++ | +++++ |
|  | 226F | +++ | + |
|  | 226G | +++++ | +++++ |
|  | 226H | +++ | ++ |
|  | 226K | +++ | + |
|  | 226L | ++++ | ++++ |
|  | 226M | ++++ | ++ |
|  | 226N | +++++ | ++++ |
|  | 226P | +++ | + |
|  | 226Q | ++++ | ++ |
|  | 226R | +++ | + |
|  | 226S | +++++ | ++++ |
|  | 226T | +++++ | +++++ |
|  | 226V | ++++ | ++++ |
|  | 226W | o | o |
|  | 226Y | ++++ | ++ |
|  | 200W-221W | +++ | +++ |
|  | 221R-226R | o | o |
|  | 200E-221E | +++ | +++ |
|  | 168E-200E-221E | o | o |
|  | 168R-221R-226R | o | o |
|  | 168W-221W-221W | o | o |
|  | 200R-221R-226R | o | o |
|  | 200E-221E-226E | o | o |
|  | 200W-221W-226W (BoNT/C1α-3W) | +++ | o |
|  | 200W-221W-226A | +++ | ++ |
|  | 200W-221W-226C | +++ | ++ |
|  | 200W-221W-226D | ++ | + |
|  | 200W-221W-226E | ++ | + |
|  | 200W-221W-226F | +++ | +++ |
|  | 200W-221W-226G | +++ | +++ |
|  | 200W-221W-226H | +++ | o |
|  | 200W-221W-226K | +++ | o |
|  | 200W-221W-226L | +++ | o |
|  | 200W-221W-226M | +++ | +++ |
|  | 200W-221W-226N | +++ | +++ |

TABLE 1-continued

Expression Assay Results for BoNT/C1 Mutants

| Domain | Mutation | Syntaxin activity | SNAP-25 activity |
|---|---|---|---|
| | 200W-221W-226P | +++ | ++ |
| | 200W-221W-226Q | +++ | +++ |
| | 200W-221W-226R | +++ | ++ |
| | 200W-221W-226S | +++ | +++ |
| | 200W-221W-226T | +++ | +++ |
| | 200W-221W-226V | +++ | +++ |
| | 200W-221W-226Y | ++ | + |
| | 168W-200W-221W-226W | o | o |
| | 168R-200R-221R-226R | o | o |
| | 168E-200E-221E-226E | o | o |
| | 200W-220W-221W-222W-226W | o | o |
| | 200W-216A-217G-218K-221W-226W | ++ | o |
| | 200W-216W-217W-218W-221W-226W | o | o |
| | 200W-216A-217A-218A-221W-226W | ++ | o |
| α-exosite | 346A | +++++ | +++++ |
| | 346E | +++++ | +++++ |
| | 346R | +++++ | +++++ |
| | 346Q | +++++ | +++++ |
| | 346W | +++++ | +++++ |
| | 365A | +++++ | +++++ |
| | 365E | +++++ | +++++ |
| | 365W | +++++ | +++++ |
| | 365R | +++++ | +++++ |
| | 365Q | +++++ | +++++ |
| | 346A-365E | +++++ | +++++ |
| | 346A-365Q | +++++ | +++++ |
| | 346A-365W | +++++ | +++++ |
| | 346A-365R | +++++ | +++++ |
| | 346E-365A | +++++ | +++++ |
| | 346Q-365A | +++++ | +++++ |
| | 346W-365A | +++++ | +++++ |
| | 346R-365A | +++++ | +++++ |
| | 346E-365E | +++++ | +++++ |
| | 346A-365A | ++++ | ++++ |
| | 346R-365R | +++++ | +++++ |
| | 316S-317delete-318delete | +++++ | +++++ |
| 250 loop-β exosite | 244N-245P-246N | +++++ | +++++ |
| | 249delete-250F-251K | +++++ | +++++ |
| | 262G-263L-264E | +++++ | +++++ |
| | 266E-267Y-268K | +++++ | +++++ |
| | 266E-267Y-268K-270I-271Y-272A | +++++ | +++++ |
| | 24I-25P-26delete | +++++ | +++++ |
| γ-exosite | 66Q-67V-68P | +++++ | +++++ |
| | 63E-64A-65K | +++++ | +++++ |
| | 59D-60D-61D | +++++ | +++++ |
| | 54E-55E-56G-57D | +++++ | +++++ |
| | 54R-55R-56R | +++++ | +++++ |
| | 54T-55Q-55N | +++++ | +++++ |
| | 54W-55W-56W | +++++ | +++++ |
| | 54A-55A-56A | +++++ | +++++ |
| | 51R-52R-53R | +++++ | + |
| | 51D-52D-53D | +++++ | + |
| | 51T-52N-53P (BoNT/C1α-51) | +++++ | o |
| | 50R-51T-52N | + | o |
| | 50Y-51T-52N | +++ | o |
| | 50D-51T-52N | + | o |
| | 51T | +++++ | ++++ |
| | 51V | +++++ | ++++ |
| | 51W | +++++ | ++++ |
| | 50D | ++ | ++ |
| | 50E | ++ | ++ |
| | 50W | ++++ | ++++ |
| | 48E | +++++ | +++++ |
| | 48N-49Q-50L | o | o |
| | 49-insertDT-50 | + | + |
| | 48-insertDT-49 | o | o |
| | 49-insertDT-50-54E-55E-56G-57D | o | + |
| | 48-insertDT-49-54E-55E-56G-57D | o | o |
| | 49K-50Y-54E-55E-56G-57D | o | o |
| | 49D-50D-54E-55E-56G-57D | o | o |
| | 49D-50-54E-55E-56G-57D | + | + |
| | 49-insertR-50-54E-55E-56G-57D | + | + |
| | 49-insertD-50-54E-55E-56G-57D | + | + |
| | 49-insertT-50-54E-55E-56G-57D | + | + |

TABLE 1-continued

Expression Assay Results for BoNT/C1 Mutants

| Domain | Mutation | Syntaxin activity | SNAP-25 activity |
|---|---|---|---|
| | 49-insertFS-50-54E-55E-56G-57D | +++++ | +++++ |
| | 51T-52N-53P-200W-221W-226W | + | o |
| | 49-insertDT-50-51T-52N-53P-54E-55E-56G-57D | o | o |
| β-paddle | 42R-43R-44R | o | o |
| | 158R-159R | o | o |
| | 170R-171R-172R | o | o |
| | 192W-193W-194W | o | o |
| | 167R-168R-169R | o | o |
| | 43R-44R | o | o |
| | 43W-44W | o | o |
| | 193W-194F | + | + |
| | 193R-194F | + | + |
| | 167Q-168F | +++ | ++ |
| | 170C-171K-172F | +++ | ++ |
| | 167Q-168F-170C-171K-172F | ++ | + |
| | 193D | ++++ | +++ |
| | 167W-168W-169W | o | o |
| putative contact regions | 119G-120delete-121delete | +++++ | +++++ |
| | 203E-204E-205S | +++++ | +++++ |
| | 135C-135I-135N | +++++ | +++++ |
| | 145delete-146delete-147Y | +++ | ++ |
| | 119G-120delete-121delete-145delete-146delete-147Y | + | + |
| | 145delete-146delete-147Y-150E-151E-152delete-153delete | o | o |
| | 200T-201F-202G | + | + |
| | 216A-217G-218K | +++ | ++ |
| | 224A-225V-226T | o | o |
| | 224A-225V-226T-235G-236H-237R | o | o |
| Bont/A chimeras | BA1-165 + BC169-430 | o | o |
| | BA1-222 + BC229-430 | o | o |
| | BA1-268 + BC276-430 | o | o |

2. Results and Discussion

We used the crystal structure of the BoNT/A_substrate complex to locate residues important for substrate recognition and specificity within the BoNT/C1 structure. We created more than 150 mutants in these and other parts of the BoNT/C1 light chain and assayed their proteolytic activity by using a lentiviral vector to introduce the encoding DNA into neurons. Western blot analysis was then used to test for proteolysis of syntaxin and SNAP-25.

Figure 1:
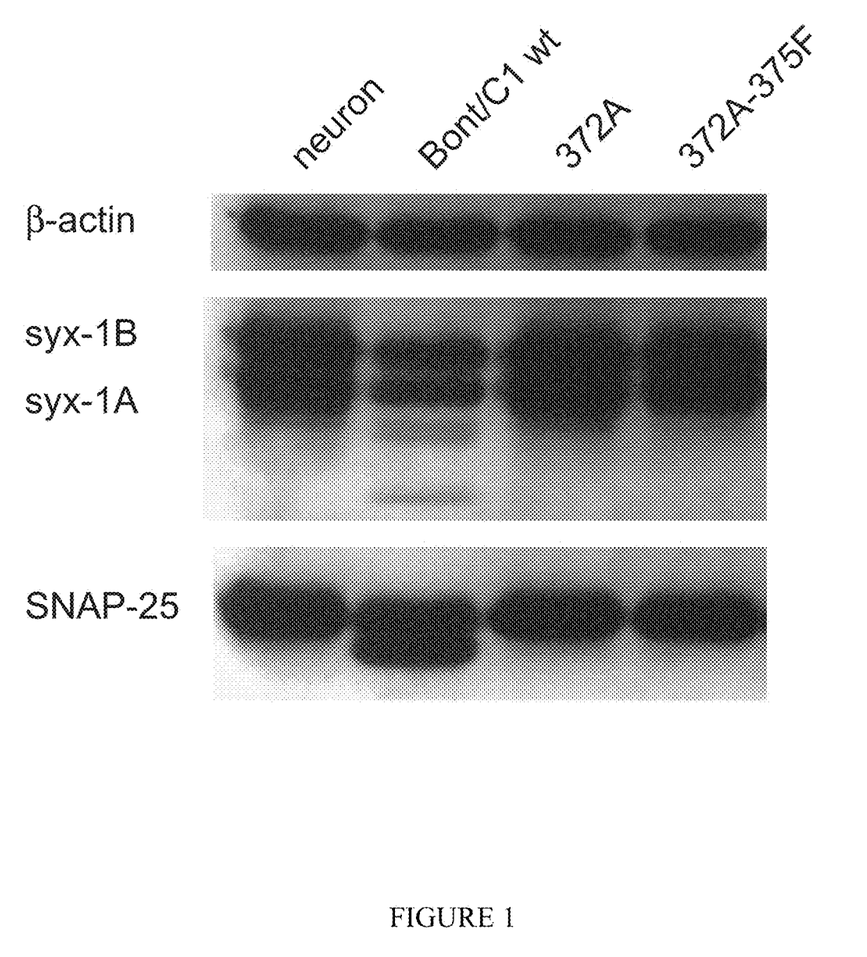
FIG. 1 shows the results of SDS polyacrylamide gel electrophoresis/western-blot analysis using antibodies against SNAP-25 and syntaxin for both uninfected cultured rat hippocampal neurons ("neuron") and cultured rat hippocampal neurons exposed to lentiviral vectors expressing wild type ("BoNT/C1 wt"; SEQ ID NO:1) and two mutant ("372A" and "372A, 375F") BoNT/C1 light chains.
Figure 2:
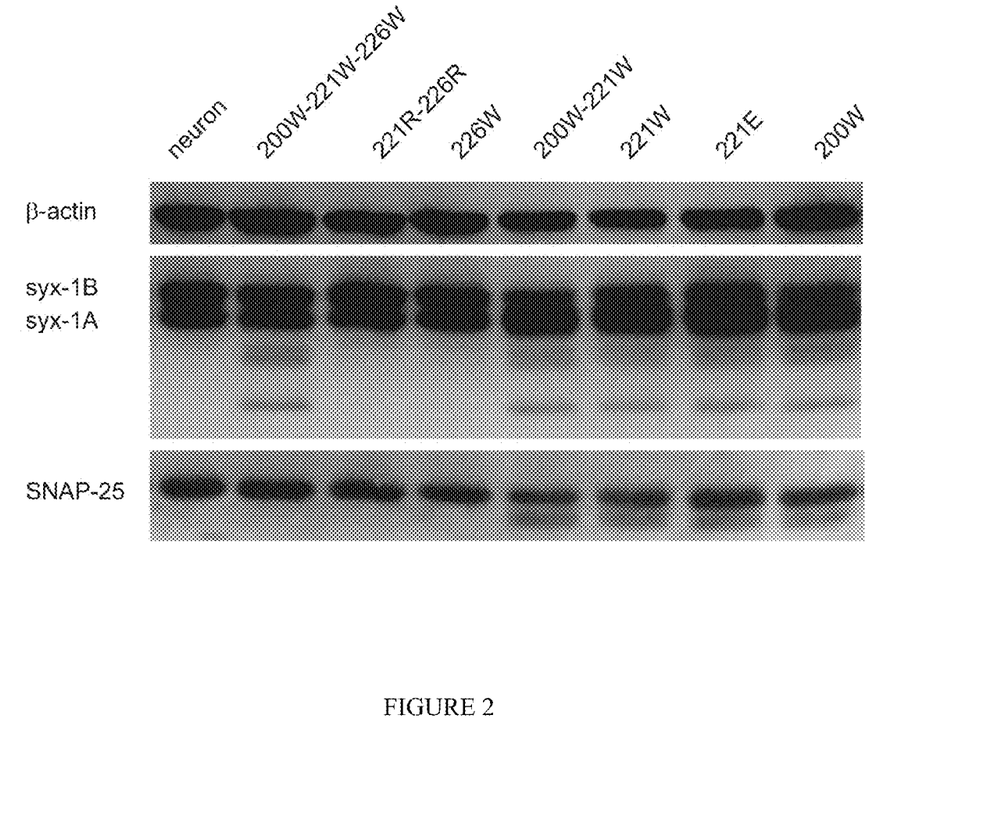
FIG. 2 shows the results of SDS polyacrylamide gel electrophoresis/western-blot analysis using antibodies against SNAP-25 and syntaxin for both uninfected cultured rat hippocampal neurons ("neuron") and cultured rat hippocampal neurons exposed to lentiviral vectors expressing seven different S1' pocket residue mutations relative to BoNT/C1 light chain (SEQ ID NO:1).
Figure 3:
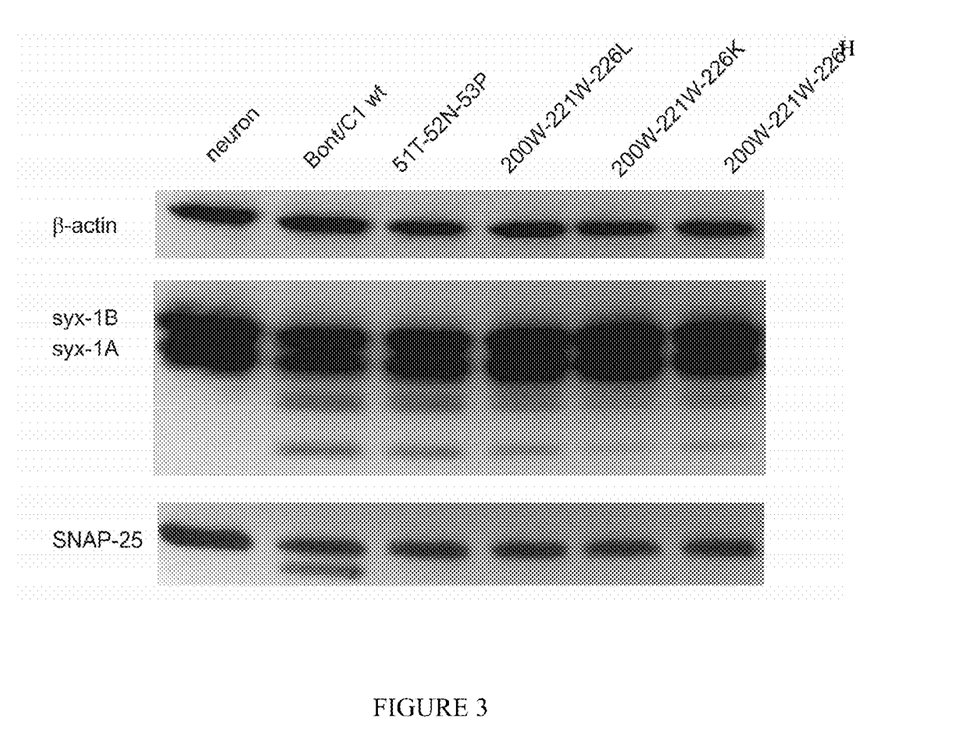

Extracts from control cells (cultured rat hippocampal neurons not transfected with a BoNT/C1 light chain) contained syntaxin 1A and 1B, which appeared as two closely spaced bands, and SNAP-25, which appeared as a single band (see lane 1, headed "neuron" in FIGS. 1, 2, and 3). Transfection with the wild-type BoNT/C1 light chain reduced the amount of full-length protein and produced lower-molecular mass cleavage products (see lane 2, headed "Bont/C1 wt" in FIGS. 1 and 2).

Most of the mutants we created exhibited dual specificity or no activity, but several were found to cleave only syntaxin and spare SNAP-25 (see, e.g., FIG. 2, lane 2; FIG. 3, lanes 3, 4, 5, and 6). Two of these highly selective mutants were designated BoNT/C1α-3W and BoNT/C1α-51. BoNT/C1R-3W was generated by mutating the three residues in the S10 pocket (L200, M221, and I226) to tryptophan. BoNT/C1α-51 was another triple mutant, 51T/52N/53P, in a region that has not previously received attention. A third mutant, the inactive form denoted BoNT/C1γ, has mutations in two critical catalytic residues (R372A and Y375F). This mutant had no proteolytic activity (see lane 4 of FIG. 1) and was used as a control for transfection and actions unrelated to catalysis.

FIG. 1 shows the detailed expression assay results for uninfected neurons (neuron), neurons infected with wild type BoNT/C1 (BoNT/C1 wt), and neurons infected with two BoNT/C1 mutants, one mutated at residue 372 (372A), and a double mutant mutated at both residue 372 and 375 (372A/375F; BoNT/C1γ). Each band of FIG. 1 indicates levels of a specific protein. In the top panel, the ~50 kD actin band (β-actin) was used as control to make sure that the cells are healthy and the amount of protein loaded is roughly the same for all of the assays. The adjacent two bands shown in the center panel represent syntaxin 1B (~34 kD) and 1A (~33 kD). In the wild type BoNT/C1 light chain experiment (labeled 'BoNT/C1 wt'), there are several bands beneath the syntaxin 1B and 1A bands. These bands indicate cleavage of these two proteins, and these cleavage bands are absent from the control experiment with no BoNT/C1 (labeled 'neuron').

Below the syntaxin results are the SNAP-25 results. Again, wild type BoNT/C1 expression gives rise to a new band (~24 kD) just under the original one (~25 kD), indicating that the SNAP-25 has been cleaved. FIG. 1 also presents results obtained with 2 BoNT/C1 mutants (372A and 372A/375F) that fail to cleave either syntaxin 1A or 1B or SNAP-25. Residues 372 and 375 are critical to forming the transition state during catalysis, and thus are essential for catalytic activity rather than substrate recognition. Mutating these residues created a 'dead' form of BoNT/C1 light chain that failed to cleave either syntaxin or SNAP-25. Our results show that these mutations do not alter substrate specificity.

FIG. 2 shows similar expression assay results for BoNT/C1 light chain mutants having amino acid substitutions in the S1' pocket region residues. These mutants had an extended cleavage incubation time of 96 hours, as compared to a 60 hour incubation time for the assays shown in FIG. 1. In general, the S1' residue mutants show decreased enzyme activity compared with wild type BoNT/C1. L200 and M221 mutants still show enzyme activity for both syntaxin and SNAP-25. I226W shows no enzyme activity for either syntaxin or SNAP-25.

Among the 150 BoNT/C1 mutants we generated, we discovered two distinct series of mutations that improve substrate specificity by restricting activity to syntaxin and sparing SNAP-25. The second lane from the left in FIG. 2 shows the expression assay results for a triple mutant member of the first such series. These mutants demonstrate the role of amino acid residues 200, 221, and 226 of the BoNT/C1 light chain, residues in a region in the catalytic cave-S1' pocket in the crystal structure. Of the various mutants of this pocket initially tested, only the triple mutant 200W-221W-226W (BoNT/C1α-3W) cleaved syntaxin but not SNAP-25. A number of other mutants in this region failed to achieve the unique specificity of cleaving only syntaxin (see FIG. 2). Although the 200W-221W-226W triple mutation recognized syntaxin but not SNAP-25, syntaxin cleavage efficiency was reduced compared to wild type BoNT/C1.

We further tested other members of the series having a triple mutation at residues 200, 221, and 226 of wild type BoNT/C1. Keeping the 200W-221W mutations of the first member of the series that was tested, we generated an additional library of 18 triple mutants in which residue 226 was mutated to one of 18 other amino acids. From this library of 18 mutants, we identified 3 additional triple mutations that only cleave syntaxin, although the protease activity was reduced to some degree. These assay results are shown in the rightmost three lanes of FIG. 3 for (from left to right) the 200W-221W-226L mutant, the 200W-221W-226K mutant, and the 200W-221W-226H mutant.

We tested another series of mutations focusing on residues 51-53, which is within the SNAP-25 substrate binding region of the BoNT/C1 light chain. This series was developed to test the result of differential binding of the substrate molecule to the BoNT/C1 light chain. Altering this region at residues 51-53 (the mutant 51T, 52N, and 53P) eliminated the ability of BoNT/C1 light chain to cleave SNAP-25, but cleavage of syntaxin was unaffected (see FIG. 3, lane labeled 51T-52N-53P). This mutant cleaves syntaxin with higher efficiency than the mutants tested in FIG. 2.

Figure 4:
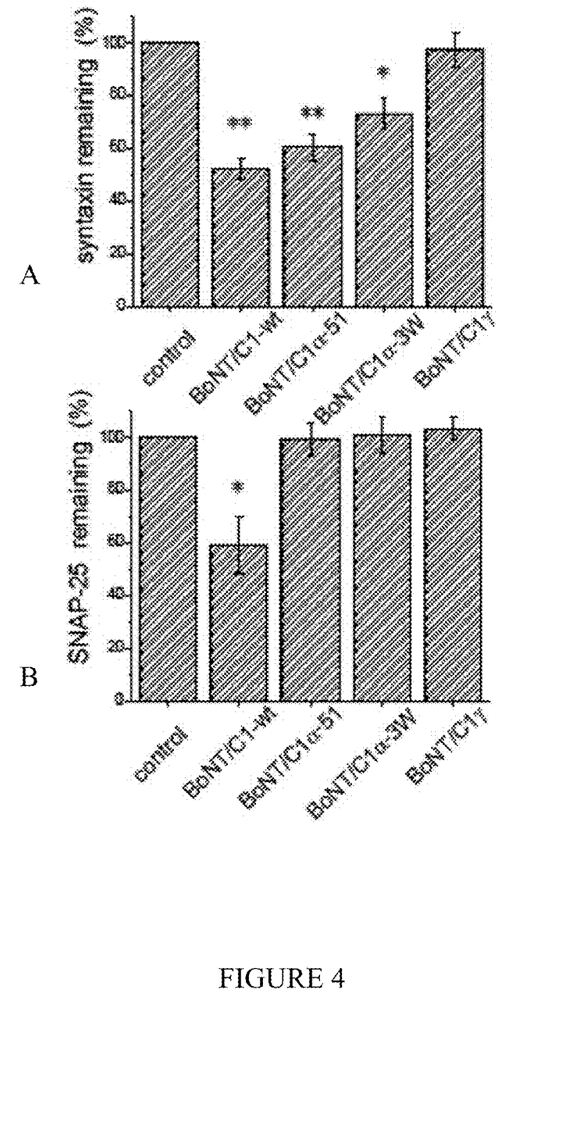

In band density gel quantification experiments, wild-type BoNT/C1, BoNT/C1α-51, and BoNT/C1α-3W reduced the syntaxin bands by 52.3, 60.5, and 73.3% of the control, respectively, while only wild-type BoNT/C1 reduced the density of the SNAP-25 band (see FIG. 4). No cleavage of synaptobrevin was seen with BoNT/C1α-51 in one experiment (data not shown). None of the many other mutants we tested exhibited such clear selectivity for syntaxin over SNAP-25.

The results from the many other mutants we generated provide further insight into structure-function relations in the BoNT/C1 light chain and its interactions with substrates. The results presented indicate the qualitative catalytic efficacy of the various mutants.

BoNT/C1 cleaves SNAP-25 between residues R198 and A199, one peptide bond before the BoNT/A cleavage site. BoNT/C1 cleaves syntaxin 1A between residues K253 and A254 and syntaxin 1B between residues K252-A253.

At least four distinct domains play important roles in the enzymatic activity of the BoNT/C1 light chain (see Jin, R., et al., *Biochemistry* 46 (2007), 10685-10693). Residues H229, H233, E269 coordinate a zinc ion to form the active site. The S1' pocket, formed by L200, M221, I226, H229, and R372, holds the substrate in position. Residues R372 and Y375 play a critical role in generating the transition state. A region we refer to as the g-exosite includes S51, R52, and N53, and is involved in substrate recognition.

The three synaptic SNAREs are cleaved by 8 different clostridial neurotoxins. In the BoNT/A light chain residues Arg362 and Tyr365 were found to be directly involved in catalysis by stabilizing the transition state (see Binz, T., et al., *Biochemistry* 41 (2002), 1717-1723). Arg(362) and Tyr(365) of the botulinum neurotoxin type A light chain are involved in transition state stabilization. By alignment with the BoNT/C1 light chain, we identified the equivalent residues Arg372 and Tyr375. We mutated one or both of these residues, and they dramatically diminished the catalytic activity of BoNT/C1 (see FIG. 1).

Since these homologous residues share similar roles, we continued to use the BoNT/A-substrate complex crystal structure to guide us in the selection of residues for mutagenesis in the BoNT/C1 light chain. BoNT/C1 recognizes the P1' sites in homologous locations in its two major substrates. In syntaxin, the P1' site is A254, and in SNAP25 the P1' site is A199. We found that the putative SP pocket of BoNT/C1 plays an important role in the proteolysis of both syntaxin and SNAP25. This most likely reflects a role for the cavity in optimizing interactions between the active site and substrate P1' site. The putative SP pocket is formed by Pro168, Leu200, Met221, Ile226, His229, Arg372. Mutations in Pro168, His229, Arg372 destroyed proteolytic activity, while mutations in Leu200, Met221 and Ile226 showed different effects. Most interestingly, as described previously, the triple mutant of 200W-221W-226W (BoNT/C1α-3W) cleaved syntaxin as well as wild type BoNT/C1 but did not cleave SNAP-25.

Based on these results, we identified a series of mutations that cleave only syntaxin (see FIGS. 2 and 3). The 200trp-221trp-226trp triple mutant (designated BoNT/C1α-3W) only cleaved syntaxin 1A and 1B, and other triple mutations having a different mutation at residue 226 showed similar selectivity for syntaxin (collectively designated BoNT/C1α forms). These results suggest that these three residues function together in substrate recognition.

However, mutations in the putative substrate binding regions, the α and β exosites, failed to alter protease activity, which suggests that substrate recognition probably depends on other sites. In the BoNT/A light chain, the '250 loop' formed antiparallel β sheets together with SNAP-25, which is important for the interaction in the β exosites (Breidenbach, M. A., et al., *Nature* 432 (2004), 925-929). However, mutations in the corresponding '250 loop' region in the BoNT/C1 light chain do not alter protease activity (see Table 1). The α exosite is thought to serve as a remote substrate binding site that places the substrate in an optimal orientation for hydrolysis. The α exosite contains residues Lys 346 and Lys 365 which could form hydrogen bonds with residues Asp 166 and Gln 152 of SNAP-25. However mutating these residues either individually or together had little or no effect on enzymatic activity (see Table 1).

We identified two regions that reduce SNARE protein cleavage, and these sites appear to have profound effects on BoNT/C1 activity. One such site is the 'paddle' region containing a sheet of four β strands. Mutating these β sheet residues completely abolished catalytic activity (see Table 1). So this region is important for both syntaxin and SNAP-25 cleavage.

We designate residues Ser51, Arg52 and Asn53 as the 'γ exosite', and propose that it has a role in SNAP-25 recognition. As discussed in more detail above, Mutating these residues to 51Thr, 52Asn and 53Pro yielded another series of syntaxin specific toxins, designated Bont/C1α-51 (see FIG. 3, lane 3). These findings reveal a number of interesting structure-function relations in the BoNT/C1 light chain, and shed light on its mechanisms of proteolytic activity and substrate recognition.

3. Summary and Conclusions.

In the data presented in this example, the inventors demonstrate the unique substrate specificity of novel mutant BoNT/C1 light chain polypeptides. Specifically, the mutants selectively cleave syntaxin while substantially or completely sparing SNAP-25. Two different lines of mutants demonstrate this substrate specificity. The first line, resulting from targeting mutations in the S1' pocket region of the BoNT/C1 light chain, includes triple mutants having a specific amino acid substitution at residues 200 and 221 (200W and 221W) and one of four possible amino acid substitutions at residue 226 (226W, 226L, 226K, 226H). The second line, resulting from targeting mutations in the SNAP-25 substrate binding region of the BoNT/C1 light chain, includes a mutant having three possible amino acid substitutions at residue 51-53 (51T, 52N, 53P). Other mutations at amino acid residues 50-53 may show similar activity.

These newly engineered BoNT/C1 light chain proteins may aid in extending the therapeutic potential of the clostridial neurotoxins. BoNT/C1 offers a potential alternative for BoNT/A in BoNT/A nonresponsive patients. Furthermore, BoNT/C1α could be useful in the treatment of diseases involving syntaxin, which has a number of functions in addition to exocytosis, including regulation of K' channels, $Ca^{2+}$ channels, and K-ATP channels. Regulation of K-ATP channels is very important in type II diabetes treatment, many cases of which are caused by hyperactive β-cells and are treated by K-ATP channel openers to limit electrical activity. Syntaxin 1A downregulates K-ATP channels to make β-cells more excitable. Cleavage of syntaxin would thus increase K-ATP channel activity to reduce the level of β-cell firing and restore normal insulin secretion. As can be appreciated, the resulting versions of BoNT/C1 with specificity for syntaxin have many potential applications in research and medicine.

Example 2

Demonstrating the Effects of BoNT/C1 Mutants on Synaptic Release in Neurons and Norepinephrine Release in Neuroendocrine Cells 1. Materials and Methods In General.

Mutants of the BoNT/C1 light chain were prepared as described in Example 1. Control cells were not transfected with mutants. Wild type BoNT/C1 is designated BoNT/C1-wt, the mutant S51T/R52N/N53P is designated BoNT/C1-α51, and the mutant L200W/M221W/I226W is designated BoNT/C1-α3W.

Cell Culture.

For primary cultured hippocampal neurons, hippocampi from E-18 embryonic rats were dissected and digested with trypsin for 30 minutes followed by trituration. The cell suspension was plated on poly-D-lysine coated cover slips in Neurobasal-A Medium (600 μl/well of a 24-well plate) together with B27 and 2 mM Glutamax, and cultured in a humidified 95% air/5% CO2 incubator. PC12 cells were cultured in DMEM, 5% horse serum, and 5% iron-supplemented calf serum in 10 cm plates at 37° C. in 90% air/10% CO2.

Electrophysiology.

Whole-cell patch clamp recordings were performed with an Axon Instruments Axopatch 200B amplifier. Cultured hippocampal neurons were bathed with an external solution containing 140 mM NaCl, 5 mM KCl, 5 mM CaCl2, 1 mM MgCl2, 10 mM HEPES, and 10 mM glucose (pH 7.4, 300 m Osm). Sylgard-coated (Sylgard 184 kit; Dow Corning, Midland, Mich.) patch electrodes were filled with 130 mM K-Gluconate, 10 mM EGTA, 5 mM HEPES, 5 mM phosphocreatine, 2 mM Mg-ATP, 0.3 mM Na-GTP (pH=7.3). EPSCs were evoked by extracellular stimulation of cultured neurons patch clamped with the same pipette solution given above but with 5 mM QX-314 (lidocaine N-ethyl bromide). For miniature EPSCs, 1 μM TTX was added to block action potentials; 50 μM D-AP5 (D-2-amino-5 phosphonopentanoate) was added to block NMDA receptors, and 100 μM picrotoxin was added to block $GABA_A$ receptors. The stimulation electrode was filled with external solution. The neurons were held at a membrane potential of −70 mV. Current was digitized with a digidata interface and read into a PC with PClamp software (Molecular Devices). Data were analyzed with MiniAnalysis software (Synaptosoft), Clampfit (Molecular Devices), and Origin (Microcal). The data were presented as the mean±SEM. The student's t-test was used to calculate the p values and presented as: p<0.01, *p<0.001.

Amperometry.

PC12 cells were loaded overnight by addition of 1.5 mM norepinephrine and 0.5 mM ascorbate to the culture medium. Cells expressing the BoNT/C1 light chain construct were selected in a fluorescence microscope using the dsRed fluorescent protein present in the syn-lox vector. Norepinephrine release was recorded with a VA-10× amperometry amplifier (ALA Scientific, Farmingdale, N.Y.) using 5-1 μm carbon fiber electrodes held at 650 mV. Cells were bathed in a solution containing 150 mM NaCl, 4.2 mM KCl, 1 mM $NaH_2PO_4$, 0.7 mM MgCl2, 2 mM CaCl2, and 10 mM HEPES (pH 7.4). Secretion was evoked by pressure ejection (for 6 seconds) from a micropipette (1-2 μm tip, ~10 μm away from the cell) of a solution identical to the bathing solution but with 105 mM KCl and 5 mM NaCl.

2. Results and Discussion

Figure 5:
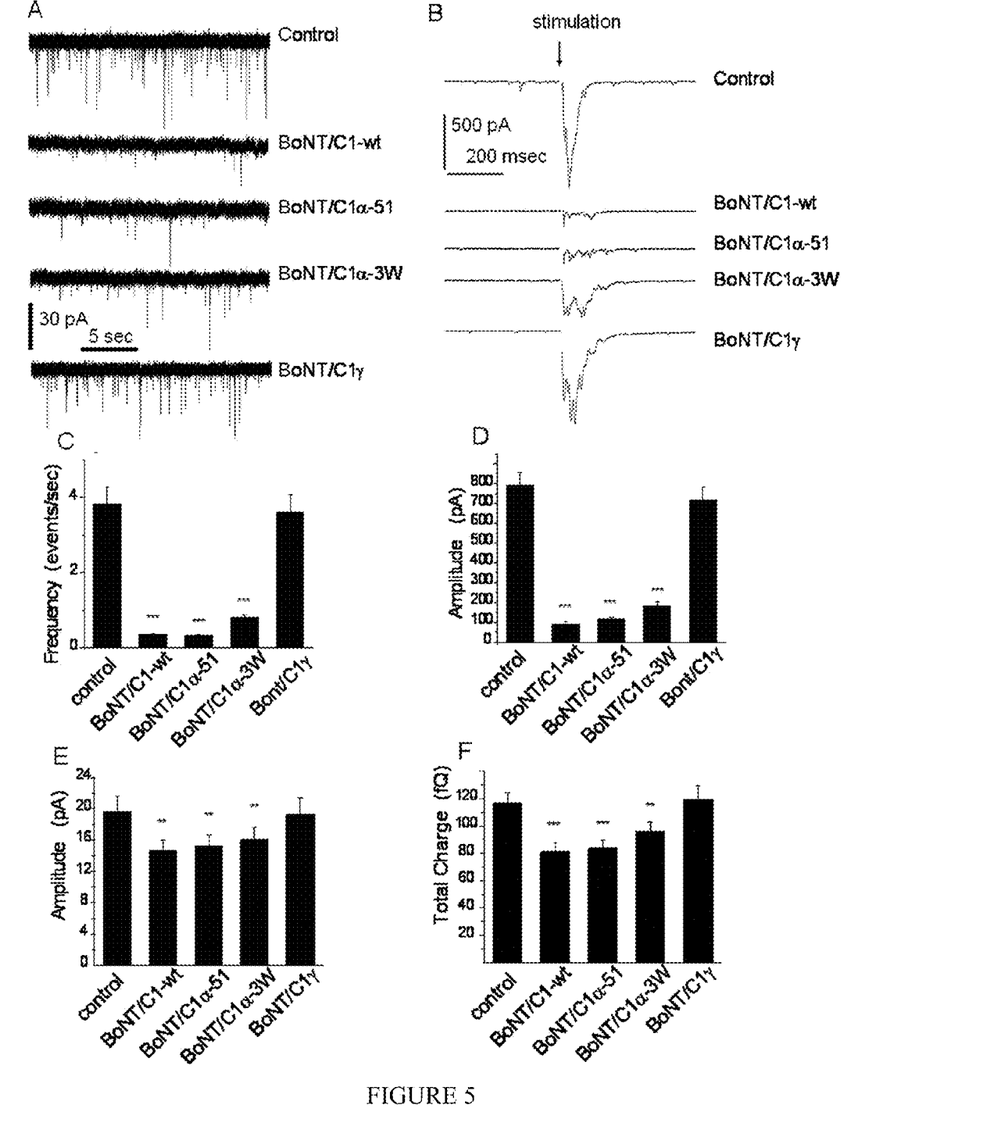
FIG. 5 shows synaptic release using patch clamp recordings from cultured hippocampal neurons 72-96 h after infection.

To evaluate the role of syntaxin in synaptic transmission, we performed patch clamp recordings from cultured hippocampal neurons expressing wild-type BoNT/C1 and BoNT/C1 mutants. Toxins effective in cleaving syntaxin reduced both miniature excitatory postsynaptic currents (mEPSCs) (FIG. 5A) and electrically evoked synaptic responses (FIG. 5B). The frequency of mEPSCs (FIG. 5C) and the amplitudes of evoked synaptic currents (FIG. 5D) were reduced approximately 10-fold below controls. BoNT/C1α-51 blocked both forms of release with a similar effectiveness, while BoNT/C1α-3W was somewhat less effective, reducing the levels of spontaneous (FIG. 5C) and evoked (FIG. 5D) release by ~5-fold. BoNT/C1γ, the inactive control, produced no significant reduction in the level of spontaneous or evoked release or quantal size (FIG. 5A-F).

The reduction in the level of synaptic transmission was greater than the reduction in syntaxin levels (compare FIG. 5A-D with FIG. 4A). This disparity has been noted previously for wild-type neurotoxins and is interpreted to mean that the exocytosis of one vesicle requires the cooperative action of multiple SNAREs.

Wild-type BoNT/C1 and the two active mutants both produced a small (~20%) but significant reduction in the amplitude of miniature synaptic currents (FIG. 5E) and charge per mEPSC (FIG. 5F), indicating that with lower levels of either syntaxin or both syntaxin and SNAP-25, the few vesicles still able to fuse are smaller and contain less glutamate. This could reflect the lower energy barrier for exocytosis of smaller vesicles, which can be overcome by the assembly of fewer SNARE complexes.

Figure 6:
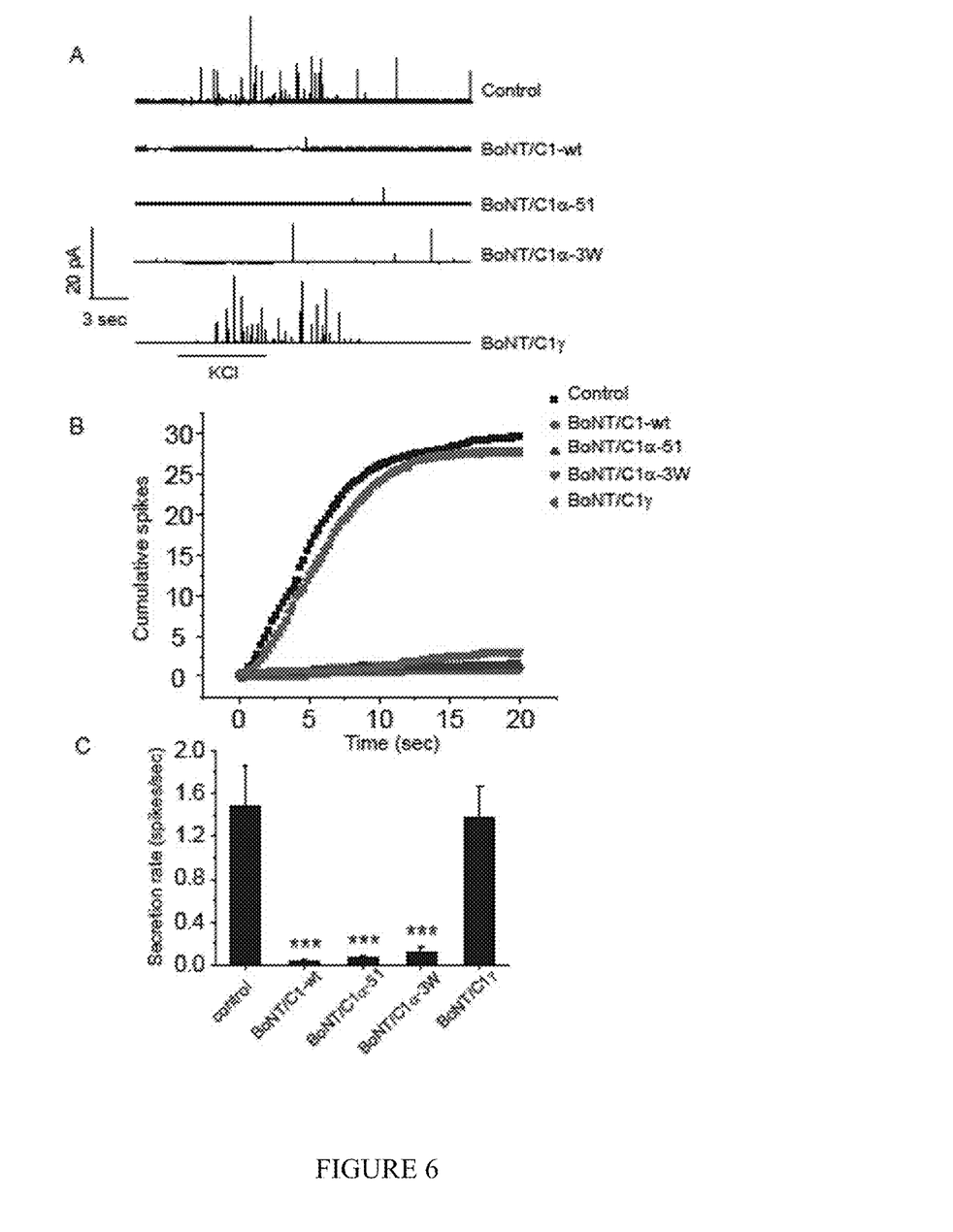
FIG. 6 shows release of norepinephrine from PC12 cells 2-3 days after transfection.

To evaluate syntaxin in the exocytosis of dense-core vesicles, we transfected PC12 cells with lentiviral vector DNA. Release was monitored using amperometry, which reveals the release of individual vesicles as spikes17 (FIG.

6A). BoNT/C1 variants that cleave syntaxin blocked depolarization-induced release of norepinephrine from PC12 cells. Depolarized PC12 cells exhibited far fewer spikes following transfection with wild type-BoNT/C1, BoNT/C1α-51, or BoNT/C1α-3W (FIG. 6A). The cumulative spike plots (FIG. 6B) and overall secretion rates (FIG. 6C) indicated a roughly 50-fold reduction; however, the action of BoNT/C1α-3W was somewhat weaker, and the control toxin BoNT/C1γ had no effect.

3. Conclusion

These experiments establish engineered versions of BoNT/C1 as tools for the acute and selective elimination of syntaxin from cells. Using these reagents, we were able to demonstrate that syntaxin is essential for $Ca^{2+}$-triggered exocytosis of synaptic vesicles in neurons and dense-core vesicles in endocrine cells. Like cleavage of SNAP-25 and synaptobrevin, cleavage of syntaxin 1A and 1B dramatically reduced the level of exocytosis. Our experiments thus place syntaxin on an equal footing with the other synaptic apparatus. Furthermore, by providing a syntaxin-free background, the engineered BoNT/C1 light chains developed for this study will serve as valuable tools for detailed studies of the mechanism by which syntaxin functions in exocytosis.

All references cited herein are incorporated by reference for all purposes. Those skilled in the art will recognize, or be able to ascertain using no more than routine experimentation, numerous equivalents to the specific materials and methods described herein. Such equivalents are considered to be within the scope of this invention and encompassed by the following claims.

---

We claim:

1. An isolated polypeptide comprising a botulinum neurotoxin C1 light chain having a modified amino acid sequence relative to the amino acid sequence of a wild-type botulinum neurotoxin C1 light chain having the amino acid sequence set forth in SEQ ID NO:1, wherein the modifications comprise:
   (a) the amino acid substitutions L200W, M221W, and I226W;
   (b) the amino acid substitutions L200W, M221W, and I226H;
   (c) the amino acid substitutions L200W, M221W, and I226K;
   (d) the amino acid substitutions L200W, M221W, and I226L;
   (e) the amino acid substitutions L200W, K216A, S217G, E218K, M221W, and I226W;
   (f) the amino acid substitutions L200W, K216A, S217A, E218A, M221W, and I226W;
   (g) the amino acid substitutions S51T, R52N, and N53P; or
   (h) the amino acid substitutions F50Y, S51T, and R52N;
   wherein the modified botulinum neurotoxin C1 light chain is capable of selectively cleaving syntaxin protein but has substantially reduced or no activity against SNAP-25, as compared to the wild-type botulinum neurotoxin C1 light chain.

2. The isolated polypeptide of claim 1, wherein the modifications comprise:
   (a) the amino acid substitutions L200W, M221W, and I226W;
   (b) the amino acid substitutions L200W, M221W, and I226H;
   (c) the amino acid substitutions L200W, M221W, and I226K;
   (d) the amino acid substitutions L200W, M221W, and I226L;
   (e) the amino acid substitutions S51T, R52N, and N53P; or
   (f) the amino acid substitutions F50Y, S51T, and R52N.

3. The isolated polypeptide of claim 2, wherein the modifications comprise:
   (a) the amino acid substitutions L200W, M221W, and I226W;
   (b) the amino acid substitutions L200W, M221W, and I226H;
   (c) the amino acid substitutions L200W, M221W, and I226K;
   (d) the amino acid substitutions L200W, M221W, and I226L; or
   (e) the amino acid substitutions S51T, R52N, and N53P.

4. The isolated polypeptide of claim 3, wherein the modifications comprise the amino acid substitutions S51T, R52N, and N53P.

5. A composition comprising the isolated polypeptide of claim 1 and a carrier.

* * * * *

SEQUENCE LISTING

```
<160> NUMBER OF SEQ ID NOS: 1

<210> SEQ ID NO 1
<211> LENGTH: 430
<212> TYPE: PRT
<213> ORGANISM: Clostridium botulinum

<400> SEQUENCE: 1

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
```

```
              260                 265                 270
Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
        290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Pro Leu Val
            420                 425                 430
```